United States Patent [19]

Leveen et al.

[11] 4,113,851
[45] Sep. 12, 1978

[54] MICROBIOCIDAL COMPOSITION AND ARTICLES PREPARED THEREFROM

[76] Inventors: Harry H. Leveen, 800 Poly Pl., Brooklyn, N.Y. 11209; Patrick J. Joyce, 103 Hubbard Ave., Stamford, Conn. 06905

[21] Appl. No.: 677,135

[22] Filed: Apr. 15, 1976

[51] Int. Cl.² .................. A61F 13/00; A61K 33/18
[52] U.S. Cl. .................................. 424/28; 424/78; 424/150; 128/156; 128/335.5
[58] Field of Search ............... 424/78, 81, 150, 28; 128/335.5

[56] References Cited

U.S. PATENT DOCUMENTS

| | | | |
|---|---|---|---|
| 3,721,652 | 3/1973 | Barnes | 260/33.4 |
| 3,984,341 | 10/1976 | Haschke et al. | 424/150 |

OTHER PUBLICATIONS

Chemical Abstracts, vol. 82 (1975), p. 86797t.

*Primary Examiner*—V. D. Turner

[57] ABSTRACT

A long acting antimicrobial and especially antibacterial composition (a) free elemental iodine (b) a polymeric linear polymer formed from the recurrence of the 2-pyrrolidone monomer

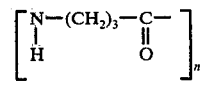

having a molecular weight of 1,000 to 500,000 and preferably wherein $n$ is sufficiently large to form a polymer having an inherent viscosity of at least 2.0 and preferably from 3.0 to 5.0 deciliters per gram. and (c) a high molecular weight isotonic acidic material preferably a polycarboxylated acid polymer such as polyacrylic acid or a polycarboxylated vinyl resin having a molecular weight of at least 10,000 and preferably between 250,000 and 300,000 gram molecular weight units. Ointments, dressings and sutures all are made from this polymer complex.

5 Claims, No Drawings

MICROBIOCIDAL COMPOSITION AND ARTICLES PREPARED THEREFROM

BACKGROUND OF THE INVENTION

One of the most medically useful agents for general germicidal, fungicidal and even viricidal application over the ages has been elemental iodine. In addition to its microbiocidal property however iodine has a second complexing property which over recent years has caused it to be complexed with a water soluble polymeric polyvinyl pyrrolidone as disclosed in Shelansky U.S. Pat. No. 2,739,922 issued in 1956. Over the past 20 years this composition of P.V.P (polyvinyl pyrrolidone) and iodine has established itself as the product of choice in bactericidal applications especially in surgery and medicine. It is used to coat the skin in preparation for surgery and as a topical ointment for wounds and burns to keep down bacterial infections.

However, Shelansky's P.V.P.-iodine complex has certain chemical and physical limitations which serve to limit its fields of application. One problem is that the use of a P.V.P.-iodine complex on a dressing or tape is not practical because the P.V.P. being water soluble in the complex can be pulled off a substrate unless it is packaged in a water proof container. A second proplem is that the time limit on the iodine microble killing power is established by the relative acidity of the wound or skin or rather the loss of the same by the generation of alkaline materials. LeVeen patent application Ser. No. 665,915 recently filed has addressed itself to the solution of the latter problem by adding to the P.V.P.-iodine complex a high molecular weight acid such as polyacrylic acid. This retards the conversion of elemental iodine to an inactive iodide salt which occurs in a basic medium. The former problem is not capable of solution so long as the pyrrolidone component of the complex is P.V.P. which is totally water soluble and thus readily gives up its bound iodine in the presence of water. A new pyrrolidone complexing agent for the reactivated elemental iodine must be found which is not water soluble yet is sufficiently reactive to iodine so that it takes the same up quickly and gives it up slowly under the preservative effect of the polymeric acid on the iodine.

OBJECTS OF THE INVENTION

It is a primary object of the present invention to describe a novel composition for iodine microbial activity which exhibits a slow release of an effective amount of elemental iodine which is protected against iodine to iodide conversion and consequent deterioration by the interaction of the alkaline environment.

It is a specific object to disclose a novel composition of (a) elemental iodine (b) a polymer of 2-pyrrolidone and (c) a high molecular weight acidic material which is isotonic to the skin and retains the composition in a long term acid enviornment.

It is a concrete object of the invention to describe a new therapeutic bandage or suture made of a polypyrrolidone-iodine- polyacrylic acid complex and a method for the manufacture of the same.

THE INVENTION

According to the present invention a new composition of matter which has prolonged germicidal properties is disclosed along with several articles manufactured therefrom such as bandages and sutures which have important uses in medicine and surgery.

This composition is made up of 3 components namely (a) elemental iodine (b) a polymer of 2-pyrrolidone as more precisely described below and (c) a polymeric poly basic acid which is isotonic to the skin and has a molecular configuration sufficient to slowly release carboxyl groups and stay free of absorption by the body tissue. A polyacrylic acid of a molecular weight of 250,000 is preferred as this third component.

The complex of iodine with the polymer of 2-pyrrolidone can be formed by reacting the elemental iodine i.e. an alcoholic tincture with an aqueous emulsion of the prepolymer of the 2-pyrrolidone of the structure:

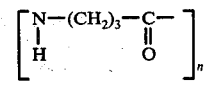

having a molecular weight of 1,000-500,000 preferably with $n$ being sufficiently great to form a polymer having an inherent viscosity of at least 2.0 deciliters per gram of polymer product, followed by dessication in a suitable dryer. If desired dry mixing can be employed to complex the iodine and the polymer however we prefer to add the two as liquids. The product so prepared has an available iodine content ranging from 8 to 15%. With the acid ingredient (c) added to this composition this level of biocidal activity of releasable elemental iodine maintains and is not converted to iodide ion as is the case with known polyvinyl pyrrolidone-iodine complexes.

The amount of acidic activity extender incorporated into the new "iodofor" composition may range from 5 to about 50 parts by weight of the total pyrrolidone-iodine composition but is preferably within a range of about 10 to 20 parts by weight of the total composition. It has been found that such a level of aciduous component is adequate to maintain the entire composition sufficiently acid after it has been in prolonged contact with a wound and the ammonia generated thereby so that the pH of the composition can be kept on the acid side of pH 7.0 and hence its bacteriocidal activity preserved.

By way of explanation it has been found that if a polypyrrolidone-iodine complex is permitted to become alkaline the germicidally active elemental iodine becomes inactivated by transfer into the form of an iodide salt. Hence since it has also been found that the use of a relatively water insoluble polypyrrolidone polymer results in a long term release of elemental iodine from the complex it is also important to insure that the iodine released into the infectious situs is maintained in a condition where it can perform its function.

The end result of the present invention is a mulifaceted medical product which can manifest itself in the shape of a salve or ointment, a dressing or bandage, a suture or several other forms all of which have the common characteristic of having long term biocidal activity. As a dressing the end product releases its active ingredients in a sustained and effective manner and obviates constant replacement of dressings and reapplication of the medication. Because the rate of release of elemental iodine from the complex is greatly extended at the same time that the biocidal activity of the released iodine is preserved the net result is a product having at least 10 and perhaps 50 times the effect of the known biocidal agents of the prior art which are currently available to the medical and surgical fields as iodine donating complexes.

The complexing of iodine with the 2-pyrrolidone polymer units is quite unexpected because there are no cyclized groups in the present polymer to hook into the iodine as is the case with the well known P.V.P. units which are currently complexed with iodine. The face that the elemental iodine is "hooked into" the polypyrrolidone polymers is demonstrated by a 3 month test of the slow release of the iodine into a starch test strip which turned blue.

The method for one preparation of the polypyrrolidone polymer components of the invention is disclosed in Barnes U.S. Pat. No. 3,721,652 granted Mar. 20, 1973. This particular polymer has sufficient viscosity to be capable of being spun into a stable formed fiber object and hence has value in the present invention where it is combined with the iodine and high molecular weight organic acids. The remarkable aspect of the Barnes polypyrrolidone referred to above is that it absorbs water but does not dissolve in it.

In an analogous manner it complexes with elemental iodine but does not release it when immersed in hot water or detergents as does P.V.P. of the known art. Consequently the polypyrrolidone-iodine complex will hold together in the presence of aqueous liquids and skin sweat and only release the iodine content at a slow sustained rate. The polyacrylic acid component can be readily absorbed into a knit fabric of the pyrrolidone polymer-iodine complex or it can be absorbed by particles of the same which are made into a gel suspension which is an acidified gel or cream dressing to be applied to burns wounds or skin infections wherever a need for a bacteriocidal or fungicidal agent is deemed to be necessary.

A preferred mode of practice of the present invention is in the formation of a new biocidal suture material. In this case a polymer of 2-pyrrolidone of the type noted above is melt spun into a continuous fiber under conventional conditions. This fiber is then dipped into a hot solution of an aqueous alcoholic tincture of iodine at a temperature of about 110° F. for about 30 seconds to one minute to take up about 15% by total weight of elemental iodine. While the suture is still warm it is dipped into a warm emulsion of polyacrylic acid of a molecular weight of about 250,000 gram molecular weight units until about 10% by weight of the polypyrrolidone-iodine complex is impregnated thoroughly with the acid. This product is then dried at room temperature to form a biocidal suture having long term activity as well as excellent tensile strength and knotting ability.

Since the suture is biocidal it may be woven into a polyfilament suture instead of a continuous monofilament suture and no surface of TEFLON or other material is needed to protect the surface of the suture from serving as the situs of a source of infection at or within the interstices of the several polypyrrolidone filaments.

Many variations on the basic concept of the present invention will occur to the reader after a consideration of the foregoing disclosure of the composition concept of the invention. All of these are contemplated and comprehended by the following several claims to the basic concept of the invention.

Concerning the acid material it must have a sufficiently high molecular weight to stay isotonic and hence ride on top of the skin or prevent absorption by the tissue and loss of its hydrogen ion donation effect. Polymer acids with free pendant carboxyl groups are ideal for this purpose as distinguished from say acetic acid or inorganic acids like phosphoric acid which will acidify the wound or burn site for a brief period of time but are shortly lost by absorption into the tissue.

As noted above polymer acids such as polyacrylic acid or a polycarboxylated cross lined vinyl resin commercially available as CARBOPOL resin 734 from the B.F. Goodrich Chemical Corp., Akron, Ohio, have been found particularly useful. These poly acid resins have a molecular weight in excess of 10,000 gram molecular weight units and preferably range about 250,000 to 300,000. The CARBOPOL has at least one half of its carbon atoms linked to carboxyl groups which can donate acidity to the wound being treated.

In addition to the water soluble polymeric acids which of course are preferred there are useful cation exchange resins which have carboxyl groups as the reacting groups thereof to counter the effects of the basic or alkaline substances which would deactivate the elemental iodine by transforming it into an iodide salt. These resins are insoluble yet they function as reactive substances which take up cations and release hydrogen ions to the composition to maintain acidity over a protracted period. These polymer acids are prepared from carboxylic acids which contain an unsaturated linkage which permits them to link into copolymers or heteropolymers with polymerizable substances. For one example styrene monomer and maleic anhydride can be polymerized and cross linked with divinylbenzene, ethylene diacrylate or diallyl maleate or fumarate. A second example is a copolymer of acrylic or methacrylic acid with any of the aforementioned cross linking monomers which are polyunsaturated polymerizable substances known for this purpose. Conventional catalysts such as benzoyl peroxide are used in known resin forming procedures. The resin powder formed is ground quite fine so as to pass a 325 mesh screen (U.S. Standard Sieve Series). These are then available as acid reactive water insoluble suspensions. They of course can be easily blended into biocidal powders, ointments or skin creams or lotions.

Whether the composition of pyrrolidone-iodine complex and resin acid are blended with petrolatum or a water soluble jelly, or used as a dry powder or talc, or as a liquid ointment or soaked or impregnated into a bandage or formed into a wound dressing or formed into a biocidal suture the principle of activity of the composition remains the same. The complex gives up its iodine slowly and that iodine stays as iodine so it gives a long term microbiocidal action.

A biocidal lotion may formulate from 50 parts by weight of a carboxylic exchange resin in acid or hydrogen form and prepared from 45 parts methacrylic acid 45 parts styrene monomer and 5 parts divinylbenzene cross linker mixed with 50 parts by weight of a polypyrrolidone-iodine complex as described above.

If an ointment base is to be added to the ingredients noted above such may be made with stearic acid, waxes spermaceti, cetyl alcohol, lanolin, mineral oils or the like dispersed in an aqueous medium with ethanolanine soap or glyceryl monostearate or monolaurate etc. or other known emulsifying and dispersing agents. The base may also contain organic compounds such as glycerine ethoxyethanol or sorbitol and/or preservatives or perfumes.

A suitable ointment base would involve a 50-50 blend with a base made from 15 parts of cetyl alcohol, one part paraffin wax, 10 parts propylene glycol, 2 parts sodium dodecyl sulfate and 72 parts of water. Alternatively 250 parts of cetyl alcohol, 250 parts of mineral oil, 120 parts of propylene glycol, 0.25 parts methyl p-hydroxy benzoate, 10 parts emulsifier and 320 parts of water may be used.

We claim as our invention:

1. A composition having prolonged microbiocidal activity containing free iodine and comprising a complex of polymeric polypyrrolidone of the structure:

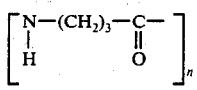

having a molecular weight of from 1,000 to 500,000 and wherein $n$ is large enough to give a polymer having an inherent viscosity of at least 0.2 deciliters per gram with a microbiocidal amount of elemental iodine and 5 to 50 percent by weight of a high molecular weight acidic activity extender having a molecular weight in excess of 10,000 up to 300,000 gram molecular weight units.

2. A composition according to claim 1 wherein the acidic activity extender is a high molecular weight polycarboxylated organic acid.

3. A composition according to claim 2 wherein the organic acid activity extender is a polyacrylic acid having a high molecular weight sufficient to make the composition isotonic to the tissue of the subject treated.

4. A biocidal suture which comprises a filament or a fiber formed from the composition of claim 1.

5. A biocidal bandage which comprises a fabric woven from a plurality of fibers derived from the composition of claim 1.

* * * * *